United States Patent [19]

Schwarz et al.

[11] Patent Number: 6,080,735
[45] Date of Patent: Jun. 27, 2000

[54] ESTRA-1,3,5(10)-TRIEN DERIVATIVES, PROCESSES FOR THEIR PREPARATION AND PHARMACEUTICAL COMPOSITIONS CONTAINING THESE COMPOUNDS

[75] Inventors: Sigfrid Schwarz, Jena; Walter Elger, Berlin; Hans-Joachim Siemann, deceased, late of Jena, by Christel Siemann, heir; by Margit Lucas, heir, Mettmann; by Frank Siemann, heir, Mitweida; Gudrun Reddersen; Birgitt Schneider, both of Jena, all of Germany

[73] Assignee: Jenapharm GmbH & Co. KG, Jena, Germany

[21] Appl. No.: 08/750,943

[22] PCT Filed: Jul. 3, 1995

[86] PCT No.: PCT/DE95/00877

§ 371 Date: Feb. 2, 1998

§ 102(e) Date: Feb. 2, 1998

[87] PCT Pub. No.: WO96/05216

PCT Pub. Date: Feb. 22, 1996

[30] Foreign Application Priority Data

Aug. 9, 1994 [DE] Germany ............... 44 29 397

[51] Int. Cl.$^7$ .................... A61K 31/58; A61K 31/56; C07J 43/00; C07J 53/00
[52] U.S. Cl. .................... 514/176; 514/182; 540/47; 540/113; 552/510; 552/539; 552/548; 552/552; 552/554; 552/555; 552/558; 552/610; 552/611; 552/618; 552/626; 552/650
[58] Field of Search ............... 540/47, 113; 552/510, 552/539, 548, 552, 554, 555, 558, 610, 611, 618, 626, 650; 514/176, 182

[56] References Cited

U.S. PATENT DOCUMENTS 5,616,574  4/1997  Reed et al. ............... 514/178

FOREIGN PATENT DOCUMENTS

| 0 430 386 | 6/1991 | European Pat. Off. . |
|---|---|---|
| 2 133 484 | 12/1972 | France . |
| 2 429 797 | 1/1980 | France . |
| 114 806 | 8/1975 | German Dem. Rep. . |
| 201 143 | 7/1983 | German Dem. Rep. . |
| 207 447 | 2/1984 | German Dem. Rep. . |
| 19 49 095 | 9/1970 | Germany . |
| 1 317 373 | 5/1973 | United Kingdom . |
| 1 398 026 | 6/1975 | United Kingdom . |
| WO 93/05064 | 3/1993 | WIPO . |
| WO 94/01450 | 1/1994 | WIPO . |

OTHER PUBLICATIONS

Schwarz et al., Steroids. XI. 17.alpha.–Ethynylestradiol Sulfamates, Z. Chem., vol. 10, No. 8, pp. 299–300, 1970.
Schwarz et al., Steroids. 15, Sulfonyloxy Derivatives of Estrogens, Pharmazie, vol. 30, No. 1, pp. 17–21, 1975.
Stoelzner et al., Dissociation of the Antigonadotrophic and the Contraceptive Activities of Certain Estratriene Derivatives, Pharmazie, vol. 30, No. 1, pp. 52–53, 1975.
Chemical Abstract for Shu et al., Structure–Activity Relationships of Estradiol Derivatives, Yao Hsueh Hsueh Pao, vol. 14, No. 6, pp. 343–348, 1979.
Howarth et al., Estrone Sulfamates Potent Inhibitors of Estrone Sulfatase With Therapeutic Potential, Journal of Medicinal Chemistry, vol. 37, No. 2, pp. 219–221, Jan. 1994.
Kalvoda et al., 7–alpha–Methylostrogene, Helvetica Chimica Acta, vol. 50, No. 1, pp. 281–288, 1967.
Uberoi et al., Structure Activity Relationships of Some Unique Estrogens Related to Estradiol Are Predicted by Fit into DNA, Steroids, vol. 45, No. 3–4, pp. 325–340, 1985.
Peters et al., 17–Desoxy Estrogen Analogues, Journal of Medicinal Chemistry, vol. 32, No. 7, pp. 1642–1652, 1989.
Bhavnani et al., Interaction of Ring–B Unsaturated Estrogens with Estrogen Receptors of Human Endometrium and Rat Uterus, Steroids: Structure, Function, and Regulation, vol. 56, No. 4, pp. 201–210, 1991.

*Primary Examiner*—Mukund J. Shah
*Assistant Examiner*—Brenda Coleman
*Attorney, Agent, or Firm*—Wood, Phillips, VanSanten, Clark & Mortimer

[57] ABSTRACT

This invention is relating to new estra-1,3,5(10)-trien-sulfamates carrying at the 3-position an R—SO$_2$—O—group, with R being an R$^1$R$^2$N—group in which R$^1$ and R$^2$, independently of each other, represent a hydrogen atom, an alkyl residue with 1–5 C atoms or, together with the N atom, a polymethylene-imino residue with 4–6 C atoms or a morpholino residue.

The compounds, according to this invention, are suitable for hormonal contraception and climacteric hormone replacement therapy (HRT) as well as for treatment of gynecological and andrological diseases. Hence, only low hepatic estrogenicity is exhibited by the compounds according to this invention.

Also described are processes for preparation of the compounds according to this invention and for preparation of pharmaceutical compositions.

3 Claims, No Drawings

ESTRA-1,3,5(10)-TRIEN DERIVATIVES, PROCESSES FOR THEIR PREPARATION AND PHARMACEUTICAL COMPOSITIONS CONTAINING THESE COMPOUNDS

This application is a Section 371 of PCT/DE95/00877, filed Jul. 3, 1995.

DESCRIPTION

This invention relates to new estra-1,3,5(10)-trien sulfamates.

Estrogens play a major role in hormonal contraception and climacteric hormone replacement therapy (HRT) as well as in the treatment of gynecological (e.g. mammary carcinoma) and andrological (e.g. prostate carcinoma) diseases.

In HRT and for contraception, estrogens are predominantly used in combination with a gestagen, e.g. levonorgestrel, desogestrel, gestodene, drospirorenone, norethisterone, cyproterone acetate, chlormadinone acetate and dienogest.

For contraception, estrogens are required for reliable suppression of follicular maturation and ovulation. They will also substitute for widely suppressed endogenic, ovarian secretion of estradiol. Such substitution is essential to maintenance of an artificial menstruation cycle and other functions of sexual organs, which would not be satisfactorily achievable by a gestagen alone.

Endogenic estrogens also have important central nervous and metabolic functions in the female organism.

Normal estrogen levels make a crucial contribution to individual comfort and wellbeing (L. Zichella; Clinical Management of the Menopausal Woman; Int. J. of Fertil. and Menop. Studies, 38, Suppl. 1 [1993], 15–22). Their presence, through various mechanisms, may help in preventing development of cardiovascular diseases, for example, by generating "favourable" lipoprotein patterns in the blood (G. Samsioe; Hormone Replacement Therapy and Cardiovascular Disease; Int. J. of Fertil. and Menop. Studies. 38, Suppl. 1 [1993], 23–29), inhibition of lipid incorporation into vascular walls (T. B. Clarkson; Experimental Effects of Progesterone versus Progestins on Arterial Wall; Gynecol. Endocrinol., 6: Suppl. 1 [1992], 15), reduction of blood pressure through favourable action on vascular tonus (R. A. Lobo; Estrogen and Cardiovascular Disease; Ann. New York Acad. Sciences, 592 [1990], 286–294), reduction of perfusion resistance in important vascular regions, attenuation of contractile stimuli on vascular muscle (C. Jiang et al.; Acute effect of 17β-estradiol on rabbit coronary artery contractile responses to endothelin-1; Am. J. Physiol., 263 [1992], H271–H275). The inner vascular walls, under the impact of estrogens, release factors (prostacyclins) which counteract to the buildup of blood clots.

Estrogens are additionally indispensable to women for preservation of the bone structure. Their loss may cause osseous degradation (osteoporosis) (C. Christiansen; Prevention and Treatment of Osteoporosis with Hormone Replacement Therapy; Int. J. of Fertil. and Menop. Studies, 38, Suppl. 1 [1993], 45–54). These latter "central nervous" and "metabolic" effects of estrogens are major aspects in HRT.

Notwithstanding the numerous appreciable aspects of estrogen therapy, there still are certain unresolved problems which impose limitations on the therapeutic use of estrogens or may entail undesirable effects.

The bioavailability of natural estrogens (estradiol, estrone, estrone sulphate, esters of estradiol, estriol) tends to be minimised after oral application (K. B. Lokind et al.; Oral bioavailability of 17β-estradiol and various ester prodrugs in the rat; Int. J. Pharmaceutics, 76 [1991], 177–182). That minimised amount is of high individual variability, and a dosage of general validity, consequently, cannot be recommended. The use of natural estrogens (estradiol) for hormonal contraception has been negatively assessed because of these pharmacokinetic restrictions (W. Kuhnz et al.; Pharmacokinetics of Estradiol, Free and Total Estrone in Young Women, following Single Intravenous and Oral Administration of 17β-Estradiol; Arzneimittel-Forschung /Drug Res., 43(II), 9 [1993], 966–973). Rapid elimination of substances from blood is another problem. Estrogen substitution in HRT must repeatedly be readjusted to the individual recipient. Efforts so far have failed to develop estradiol prodrugs for improved oral bioavailability (K. B. Lokind et al.; see above).

Synthetic estrogens, too, are accompanied by serious drawbacks. Ethinyl estradiol (EE) is the most important synthetically modified estrogenic steroid. It is an estrogen that plays a predominant role in oral hormonal contraception. Apart from EE, mestranol is used in few cases, a "prodrug" which is metabolised to EE in the organism (J. W. Goldzieher; Selected aspects of the pharmacokinetics and metabolism of ethinyl estrogens and their clinical implications; Am. J. Obstet. Gynecol., 163 [1990], 318–322). EE, when orally applied (to a human recipient), is much better in bioavailability than the aforementioned natural estrogens, although its oral bioavailability may drastically decline, depending on the individual recipient. Goldzieher, in the context of pharmacodynamics, stressed the negative consequences implied in the variability of the area under the curve (AUC) as well as variability of half-life and time passing until maximum blood levels were reached. The highest AUC recorded from his study, 0–24 hours from application, amounted to 2121 pg×h/ml. The lowest AUC was 284 pg×h/ml. A similar scatter of AUC, around the factor 6 to 7, was described by Hurmpel et al. (M. Hümpel et al.; Comparison of Serum Ethinyl Estradiol, Sex Hormone-Binding Globulin, Corticoid-Binding Globulin and Cortisol Levels in Women Using Two Low-Dose Combined Oral Contraceptives; Horm. Res., 33 [1990], 35–39).

The route taken by orally applied active substances, following absorption, is from the intestinal lumen via liver into the organism. This fact is of particular relevance to estrogenic substances, as the liver is a success organ for estrogens, and their oral administration thus may lead to strong intrahepatic estrogenic effects. Secretional activities regulated by estrogens in the human liver include synthesis of transport proteins, CBG, SHBG and TBG, angiotensinogen, various factors that play a major physiological role in blood coagulation, and lipoproteins.

If, however, natural estrogens are fed to the female organism by bypassing passage through the liver, say, by transdernal application, the above liver functions will not be affected and will stay unchanged (U. Larsson-Cohn et al.; Some biochemical consequences of post-menopausal hormone replacement treatment; in: The Controversial Climacteric, Ed.: P. A. van Keep et al.; MTP Press Ltd. [1982]). Oral administration of therapeutically equivalent doses of natural estrogens leads to unambiguous response by various hepatic parameters: rise of SHBG, CBG, angiotensin, HDL (high-density lipoproteins) (J. C. Stevenson et al.; Oral versus Transdermal Hormone Replacement Therapy; Int. J. of Fertil. and Menop. Studies, 38 Suppl. 1

[1993], 30–35). Hepatic estrogen effects resulting from equine estrogen mixtures (socalled conjugated estrogens) were clearly found to be more strongly pronounced than those attributable to natural estrogens (C. A. Mashchak et al.; Comparison of pharmacodynamic properties of various estrogen formulations; Am. J. Obstet. Gynecol., 144 [1982] 511–518). Even stronger hepatic estrogenicity may be attributed to ethinyl-estradiol and DES. Related to antigonadotropic properties, the estrogenic effectiveness of EE in the liver is eight to ten times as high as that of orally administered natural estrogens. Hence, there is a highly unfavourable dissociation of properties (B. von Schoultz et al.; Estrogen Therapy and Liver Function—Metabolic Effects of Oral and Parenteral Administration; The Prostate, 14 [1989], 389–395).

The following observation shows that undesirable hepatic estrogen effects cannot be avoided by dose reduction of EE in contraceptives. Reduction from 30 μg to 20 μg EE, either dose in combination with 150 μg of the same gestagen, did not result in reduction, after three months, of considerably increased angiotensin levels and gave, at best, marginally reduced values after six months (A. Basdevant et al.; Hemostatic and metabolic effects of lowering the ethinyl-estradiol dose from 30 mcg to 20 mcg in oral contraceptives containing desogestrel; Contraception, 48 [1993], 193–204).

Fatal thromboembolic complications are known to be a real problem in the context of high-dosage estrogen therapy of men for prostate carcinoma (B. von Schoultz et al.; loc.cit.).

The strategy of oral hormonal contraception is determined in a somewhat subdued manner by potential side-effects of EE in the liver.

Given the need for contraceptive effectiveness together with preservation of regular menstruation, on the one hand, and the high potential of side-effects, on the other, the difficulty of controlling desired EE blood levels means a severe problem comparable to a tightrope walking exercise. A considerable percentage of women may not be in a position of using oral contraceptives because their theshold of acceptance is exceeded by menstrual abnormalities or estrogen-related side-effects.

The risk of cardiovascular diseases, even with fatal outcome, clearly tends to grow in response to hormonal contraceptives (V. Wynn; Oral contraceptives and coronary diseases; J. Reprod. Med., 36, Suppl. 3 [1991], 219–225). Some of the risk factors depend on age (J. I. Mann; Oral contraceptives and myocardial infarction in young women; Pharmacol. Steroid. Contracept. Drugs, Eds.: S. Garrattini and H. W. Berendes, Raven Press, New York [1977], 289–296). Several health authorities, therefore, have warned against the use of hormonal contraceptives by women beyond the age of 35 years. The risk of contracting a cardiovascular disease is even greater for smoking female users of hormonal contraceptives beyond 35 (F. A. Leidenberger; Klinische Endokrinologie fur Frauenärzte; 382–383; J. I. Mann, loc.cit.). The risk of fatal cardiovascular diseases in users of oral contraceptives was found to be five to six times higher than in control populations (F. A. Leidenberger; loc.cit.). These data provide evidence to the effect that there are sizeable sub-groups of sexually mature women to whom conventional hormonal contraceptives can be applied only with an unjustifiably high risk or must not be applied at all.

Latest research suggests that the above problems should be attributed to the estrogen component of hormonal contraceptives rather than to the gestagen component (Skouby et al.; J. Obstet. Gynecol. [1990], 1535–1537). At a "consensus meeting", the conclusion was drawn that the real risk of fatal myocardial infarction did not depend on the length of use. These findings seemed to confirm that fatal clotting was not attributable to chronic damage to arterial walls in the heart (arteriosclerosis) but to acute effects upon hemostatic functions in the liver (R. A. Lobo; loc.cit.). Hence, reduction of estrogen effects on the liver appears to be a way to eliminate the above risks of hormonal contraception and the associated restrictions on applicability.

The risks described in the context of EE are explicitly ruled out for natural estrogens, i.e. estrogens of hepatic estrogenicity lower than that of EE (R. A. Lobo; loc.cit.).

Individual adaptation of dosage is generally required for HRT, using natural hormones on the basis of latest technology. Treatment, in this context, has proved to be accompanied by major uncertainties relating to the risk of overdosage or underdosage.

This invention, consequently, has been made for the purpose of providing estra-1,3,5(10)-trien derivatives which do not exhibit the above detrimental characteristics and side-effects.

This purpose is met, according to the invention, by providing estra-1,3,5(10)-trien derivatives in conformity with the general Formula I

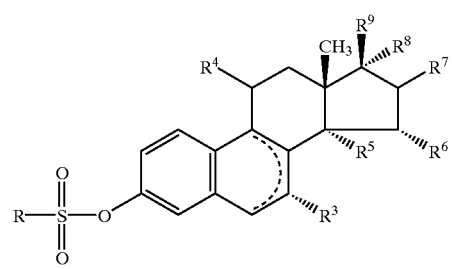

(I)

where R is an $R^1R^2N$ group, in which $R^1$ and $R^2$, independent of each other, represent a hydrogen atom, a $C_1$–$C_5$ alkyl residue or, together with the N atom, a polymethylene-imino residue with 4 to 6 C atoms or a morpholine residue, with $R^3$ being a hydrogen atom or an alkyl group with 1–5 C atoms, with $R^4$ being a hydrogen atom, a hydroxy group, an esterified hydroxy group, a haloalkyl group with 1–5 C atoms or an alkoxy group with 1–5 C atoms, $R^5$ and $R^6$ being a hydrogen atom each or, together, being a methylene group, $R^7$, $R^8$ and $R^9$, independent of each other, representing a hydrogen atom or a hydroxy group, and ring B containing one or two double bonds or $R^8$ representing an alkinyl residue with up to 5 carbon atoms or $R^8$ and $R^9$ together representing an oxygen atom or $R^5$ and $R^8$ being a vinylene or ethylene group.

The estra-1,3,5(10)-trien derivatives, according to this invention, which carry an R—$SO_2$—O grouping at the C atom 3 and in which R plays the role described above may contain additional double bonds between C atoms 6 and 7, 7 and 8, 8 and 9, 9 and 11, 8 and 14, 14 and 15 and/or 15 and 16.

The estra-1,3,5(10)-trien derivatives, according to this invention, which carry an R—$SO_2$—O grouping at the C atom 3 and in which R plays the role described above may contain oxo-goups at C atoms 6, 7, 11, 15, 16 and/or 17.

The estra-1,3,5(10)-trient derivatives, according to this invention, which carry an R—$SO_2$—O grouping at the C atom 3 and in which R plays the role described above may carry additional hydroxy groups at C atoms 6, 7, 9, 11, 14, 16 and/or 17, and these hydroxy groups may be esterified or etherified.

Such esterification will be through common derivatives of physiologically compatible inorganic or organic acids. These may be phosphoric acid, sulphuric acid, oxalic acid, maleic acid, fumaric acid, lactic acid, tartaric acid, malic acid, citric acid, salicylic acid, valeric acid, adipic acid and benzoic acid. More applicable acids may be seen, for example, from "Fortschritte der Arzneimittelforschung", Vol. 10, pp. 224–225, Birkhäuser Verlag, Basel and Stuttgart, 1966, and Journal of Pharmaceutical Sciences, Vol. 66, pp. 1–5 (1977). Etherification is achieved by means of common derivatives of aliphatic alcohols with up to six carbon atoms.

The estra-1,3,5(10)-trien derivatives, according to this invention, which carry an R—$SO_2$—O grouping at the C atom 3 and in which R plays the role described above may be substituted at C atoms 6, 7, 11, 14, 15, 16 and/or 17 by alkyl residues, alkylidene residues, alkenyl residues and alkinyl residues with up to five carbon atoms, and these residues, in turn, may be substituted in the same manner by alkyl, alkylidene, alkenyl or alkinyl residues or halogen.

The estra-1,3,5(10)-trien derivatives, according to this invention, which carry an R—$SO_2$—O grouping at the C atom 3 and in which R plays the role described above may be substituted by alkylene residues or alkenylene residues with up to three carbon atoms between C atoms 14 and 15 or 14 and 17.

3-sulfamate-estra-1,3,5(10)-trien derivatives, according to this invention which carry an R—$SO_2$—O grouping at the C atom 3 and in which R plays the role described above, for example, may be as follows:

17β-hydroxy-14α,15α-methylene-estra-1,3,5(10)-trien-3-yl N,N-dimethylsulfamate,
17β-hydroxy-14α,15α-methylene-estra-1,3,5(10)-trien-3-yl N,N diethylsulfamate,
17β-hydroxy-14α,15α-methylene-estra-1,3,5(10)-trien-3-yl pyrrolidinosulphonate,
17β-hydroxy-14α,15α-methylene-estra-1,3,5(10)-trien-3-yl morpholinosulphonate,
17β-hydroxy-14α,15α-methylene-estra-1,3,5(10)-trien-3-yl N-methylsulfamate,
17β-hydroxy-14α,15α-methylene-estra-1,3,5(10)-trien-3-yl sulfamate,
17β-hydroxy-14α,15α-methylene-estra-1,3,5(10), 7-tetraene-3-yl N,N-dimethylsulfarmate,
17β-hydroxy-14α,15α-methylene-estra-1,3,5(10), 6,8-pentaene-3-yl N,N-diethylsulfamate,
17β-hydroxy-14α,15α-methylene-estra-1,3,5(10), 8-tetraene-3-yl N,N-dimethylsulfamate,
11β-chloromethoxy-17β-hydroxy-estra-1,3,5(10)-trien-3-yl N,N-dimethylsulfamate,
17β-hydroxy-14α,15α-vinylene-estra-1,3,5(10)-trien-3-yl N,N-diethylsulfamate,
14α,17α-ethylene-17β-hydroxy-estra-1,3,5(10)-trien-3-yl pyrrolidinosulphonate,
16α,17β-dihydroxy-14α,17α-ethylene-estra-1,3,5(10)-trien-3-yl N,N-diethylsulfamate,
17β-hydroxy-7α-methyl-estra-1,3,5(10)-trien-3,11β-diyl 3-N,N-dimethylsulfamate-11-nitrate,
17β-hydroxy-11β-methoxy-19-nor-17α-pregn-1,3,5(10)-trien-20-in-3-yl N,N-dimethylsulfamate,
17β-hydroxy-19-nor-17α-pregn-1,3,5(10)-trien-20-in-3-yl-sulfamate,
17β-hydroxy-19-nor-17α-pregn-1,3,5(10)-trien-20-in-3-yl N-methylsulfamate,
17β-hydroxy-estra-1,3,5(10),7-tetraene-3-yl N,N-diethylsulfamate,
17β-hydroxy-estra-1,3,5(10),6,8-pentaene-3-yl N,N-dimethylsulfamate,
17α-hydroxy-14α, 15α-methylene-estra-1,3,5(10)-8-tetraene-3-yl sulfamate,
17-oxo-estra-1,3,5(10)-trien-3-yl N-methylsulfamate,
17-oxo-estra-1,3,5(10)-trien-3-yl sulfamate,
11β-methoxy-17-oxo-estra-1,3,5(10)-trien-3-yl sulfamate,
17β-hydroxy-estra-1,3,5(10)-trien-3-yl N-methylsulfamate,
17β-hydroxy-estra-1,3,5(10)-trien-3-yl sulfamate,
17β-hydroxy-estra-1,3,5(10), 6,8-pentaene-3-yl sulfamate,
17α-hydroxy-estra-1,3,5(10)-trien-3-yl sulfamate,
estra-1,3,5(10)-trien-3, 17β-diyl 3-sulfamate, 17-pentanoate,
estra-1,3,5(10)-trien-3, 17β-diyl 3,17-sulfamate,
16α,17β-dihydroxy-estra-1,3,5(10)-trien-3-yl N,N-diethylsulfamate,
16α,17β-dihydroxy-estra-1,3,5(10)-trien-3-yl N,N-dimethylsulfamate,
16α,17β-dihydroxy-estra-1,3,5(10)-trien-3-yl morpholinosulphonate,
16α,17β-dihydroxy-estra-1,3,5(10)-trien-3-yl N-methylsulfamate,
16α,17β-dihydroxy-estra-1,3,5(10)-trien-3-yl sulfamate,
11β-chloromethoxy- 17β-hydroxy-estra-1,3,5(10)-trien-3-yl sulfamate,
17β-hydroxy-14α,17α-vinylene-estra-1,3,5(10)-trien-3-yl sulfamate,
14α,17α-ethylene-17β-hydroxy-estra-1,3,5(10)-trien-3-yl N-methylsulfamate
16α,17β-dihydroxy-14α,17α-ethylene-estra-1,3,5(10)-trien-3-yl sulfamate,
17β-hydroxy-7α-methyl-estra-1,3,5(10)-trien-3, 11β-diyl 3-sulfamate-11-nitrate,
17β-hydroxy-11β-methoxy-19-nor-17α-pregn-1,3,5(10)-trien-20-in-3-yl sulfamate Particular preference is given also to estra-1,3,5(10)-trien derivatives of the general Formula I, with $R^7$ and $R^9$ standing for hydroxy groups.

Particular preference is given to estra-1,3,5(10)-trien derivatives of the general Formula I, with $R^5$ and $R^6$ together representing an ethylene or methylene group.

The following estra-1,3,5(10) derivatives, according to this invention, are particularly preferred:

17β-hydroxy-14α,15α-methylene-estra-1,3,5(10)-trien-3-yl N,N-diethylsulfamate,
16α,17β-dihydroxy-estra-1,3,5(10)-trien-3-yl N,N-dimethylsulfamate,
17β-hydroxy-14α,15α-methylene-estra-1,3,5(10)-trien-3-yl N,N-dimethylsulfamate and
16α,17β-dihydroxy-estra-1,3,5(10)-trien-3-yl N,N-diethylsulfamate.

This invention is, furthermore, related to a process for the production of estra-1,3,5(10)-trien derivatives according to the invention and which is characterised by conversion of an estra-1,3,5(10)-trien derivative in a generally known way with an appropriately substituted amidosulphonyl chloride by esterification of the 3-OH group of the estra-1,3,5(10)-trien derivative.

Conversion is generally carried out in a two-phase system in the presence of a quarternary ammonium salt which acts as phase transfer catalyst. Conversion temperatures are between room temperature and 100° C. Common two-phase systems used as solvents, such as chloroform-water, dichloromethane-water, toluene-water etc.

Another subject of this invention is relating to pharmaceutical compositions which contain estra-1,3,5(10)-trien derivatives of the general Formula I as active substance, with these compositions possibly containing adjuvants and carriers as may be required.

The pharmaceutical compositions, according to this invention, may additionally contain one or more of the aforementioned gestagens, such as levonorgestrel, desogestrel, gestodene, drospirorenone, norethisterone, cyproterone acetate, chlormadinone acetate or dienogest.

The pharmaceutical compositions, according to this invention, may as well be provided in the form of multi-stage or combination products.

The combination product for contraception, for example, consists of a first stage which may be a combination of several components, namely a biogenic estrogen, a synthetic estrogen, a gestagen and/or an estra-1,3,5(10)-trien derivative, according to this invention, and one or several additional stages which may consist of a pharmaceutically safe placebo or a biogenic or synthetic gestagen or a biogenic or synthetic estrogen or an estra-1,3,5(10)-trien derivative, according to this invention, or a combination of several components, namely a biogenic estrogen, a synthetic estrogen, a gestagen, an estra-1,3,5(10)-trien derivative, according to this invention, or a combination of synthetic estrogens or an estra-1,3,5(10)-trien derivative, according to this invention, and a gestagen.

The biogenic estrogen, for example, possesses a component of the group of estradiol, estrone, estrane, estriol and other biogenic estrogens or at least one compound which rapidly makes one of the aforementioned estrogen components split off immediately after taking.

The synthetic estrogen, according to this invention, possesses at least one component of the group of ethinyl estradiol, mestranol and other synthetic estrogens or at least one compound which rapidly makes one of the aforementioned estrogen components split off immediately after taking.

The gestagen, according to this invention, possesses at least one component of the group of levonorgestrel, desogestrel, progesterone, norethisterone acetate, chlormadinone acetate, gestodene, cyproterone acetate and other natural and/or synthetic gestagens or at least one compound which rapidly makes one of the aforementioned gestagen components split off immediately after taking.

Another subject of this invention is relating to ways of providing pharmaceutical compositions which may be used for hormonal contraception, climacteric hormone substitution therapy and treatment for gynecological and andrological diseases, such as mammary carcinoma and prostate carcinoma.

Another subject of this invention is relating to pharmaceutical compositions in the form of tablets, tablets for controlled release, coated tablets, pills, capsules, film tablets and film tablets for controlled release.

The pharmaceuticals are manufactured in generally known and established processes in conformity with desired modes of application and in appropriate dosage, using common solid or liquid carriers or diluents and common pharmaceutical adjuvants. Preference is given to formulations for oral application. Such formulations may be tablets, film tablets, coated tablets, capsules, pills, powder or depot preparations.

Appropriate tablets, for example, may be obtained be intermixing of the active substance with known adjuvants, such as inert diluents like dextrose, sugar, sorbitol, mannitol, polyvinylpyrrolidone, blasting agents like corn starch or alginic acid, bonding agents like starch or gelatin, lubricants like magnesium stearate or talc and/or agents by which to achieve a depot effect, such as carboxylpolymethylene, carboxylmethyl cellulose, cellulose acetate phthalate or polyvinyl acetate. The tablets may as well be made up of several layers.

Coated tablets can be made, accordingly, by coating cores made in analogy to tablets, using common coating agents, such as polyvinylpyrrolidone or shellac, gum arabic, talc, titanium dioxide or sugar. The coat may consist of several layers, and the adjuvants mentioned in the context of tablets may be used.

Capsules with active substances in them, for example, may be manufactured by intermixing the active substance with an inert carrier, such as lactose or sorbitol, and encapsulating it in gelatin capsules.

However, in view of the severe drawbacks of conventional estrogen derivatives used for medical purposes, an urgent demand has come up for compounds without those drawbacks.

The compounds, according to this invention, were surprisingly found to be superior to EE with regard to estrogenic efficacy, accompanied by maximum genital estrogen effects in the uterus and hepatic estrogenicity not stronger than that of estradiol, the natural estrogen. This constellation, as provided by the compounds according to this invention, will bring about substantial improvement in therapeutic properties, as compared to natural and synthetic estrogens.

Contraceptives containing the estra-1,3,5(10)-trien derivatives, according to this invention, are likely to enable total redefinition of restrictions on the use of hormonal contraception, since they are less effective or not effective at all on the hemostatic system.

Contraceptives containing the estra-1,3,5(10)-trien derivatives, according to this invention, on account of their dramatically reduced estrogen effects, may be applied in doses high enough for cycle control better than that achievable by means of conventional EE contraceptives.

The use of EE in hormone substitution therapy at present is strictly rejected because of the side-effects involved. The risks implied in non-natural (biogenic) estrogens have ceased to exist with the advent of the estra-1,3,5(10)-trien derivatives according to this invention. Different from the natural estrogens which are predominant in hormone substitution therapy today, an advantage is provided by significantly superior controllability, as oral bioavailability is clearly defined and is no longer burdened with the major individual variability of biogenic estrogens.

Evidence was provided to hepatic estrogenicity in ovariectomised rats: The adult female experimental animals (breeder: HSD/WIN:WU) were ovariectomised (Day 14). Treatment with one daily oral application of test substances was started two weeks after ovariectomy.

All animals were assigned to groups by randomised approach. The experiment was a block design. All animals were weighed twice, prior to and at the end of the experiment.

Start and end of treatment were defined as Day 1 (=d1) or Day 7 (=d7). The animals were sacrificed on Day 8. Several organs (uterus, adrenal glands, liver) were removed and weighed and were passed on in deep-frozen condition (−196° C.) for further investigation.

Blood was taken from the retrobulbar plexus prior to treatment (d0) as well as on (d4) and (d8), with the animals etherized. The serum thus obtained was used to determine $IGF_1$, angiotensin I, cholesterol and HDL cholesterol.

Methods of determination:

$IGF_1$—RIA bioMérieux Co.;

Angiotensin—modified RIA for renin activity—Sorin Co.;

Cholesterol/HDL—enzymatic tests, photometry, reagents supplied from Dr. Bruno Lange GmbH.

The results obtained from the assays are given in Table 1.

Orally applied estra-1,3,5(10)-trien derivatives, according to this invention, for uterine efficacy, are equivalent or superior to ethinyl estradiol (EE). Also, effects on parameters of hepatic estrogenicity are absent or are significantly lower than those of comparable doses of ethinyl estradiol (EE).

The blood levels of estra-1,3,5(10)-trien derivatives, according to this invention, are much higher than those of the comparable substances, estradiol (E2), ethinyl estradiol (EE) and estriol (E3).

TABLE 1

| | Oral estrogen effects Impact on sexual function and hepatic parameters | | | | | |
|---|---|---|---|---|---|---|
| Substance | Dosage/d µg/ animal p.o. | Uterus weight (mg) | Total cholest. (mg/dl plasma) | HDL cholest. (mg/dl plasma) | Angiotensin I (ng/mg plasma) | Blood level (pg/ml (serum) |
| Estradiol (E2) | 10 | 182 | 84.3 | 54.1 | 344.6 | 19.2 |
| Ethinyl estradiol (EE) | 10 | 353 | 41.9 | 24.3 | 639.6 | 28.9 |
| Estriol (E3) | 10 | 302 | 70.9 | 42.7 | 495.9 | 8.815 |
| J 983 | 10 | 349 | 75.5 | 48.3 | 413.2 | 33.2 |
| J 989 | 10 | 183 | 95.8 | 52.5 | 412.9 | 42.875 |
| J 982 | 10 | 193 | 83.3 | 50.8 | 421.5 | 46.4 |
| J 984 | 10 | 246 | 89.6 | 47.8 | 405.3 | 75.8 |

The invention is explained by the following examples.

EXAMPLE 1

General manufacturing specifications for N,N-disubstituted 3-sulfamates of estra-1,3,5(10)-trien derivatives.

The estra-1,3,5(10)-trient derivative earmarked for esterification, amidosulfonylchloride, alkali hydroxide or alkaline-earth hydroxide as well as quarternary ammonium salt as phase transfer catalyst are added under vigorous agitation to a mixture of an appropriate organic solvent and water. Agitation is continued until full completion of esterification is signalled by analytical evidence (thin-layer chromatography), with working temperatures between 50° C. and 100° C. being permissible, as shortening of reaction time may be desired. The two phases then are separated from each other. The aqueous phase is re-extracted, and the unified organic extracts are consecutively washed in diluted hydrochloric acid, saturated sodium hydrogencarbonate solution and water. The extract then is dried over anhydrous sodium sulphate and is evaporated under reduced pressure for dryness. The residue is recrystallised from an appropriate solvent.

EXAMPLE 2 (=J 983)

Preparation of 17β-hydroxy-14α,15α-methylene-estra-1,3,5(10)-trien-3-yl N,N-diethylsulfamate 2 g of 14α,15α-methylene-estra-1,3,5(10)-trien-3, 17β-diol are suspended in 30 ml of toluene, 4 ml of water, 0.32 g of benzyltriethylammonium chloride, 2.94 ml of N,N-diethylamidosulphonyl chloride and 2.1 ml of 40% sodium hydroxide solution and are agitated and heated for two hours to an intrinsic temperature of 80° C.

Cooling to room temperature is followed by processing as described in Example 1. The crude product thus obtained is chromatographed to silica gel (particle size: 0.063 to 0.2 mm). The title compound is obtained, following elution in chloroform/ethyl acetate 9:1 and recrystallisation from methanol. Melting point: 68–73°C.; $^1$H-NMR: 0.26 (m, CH$_2$), 0.99 (s, 18-H), 3.38 (q, 7.2 Hz, CH$_3$—CH$_2$—N), 3.55 (dd, E16 Hz), 7.31 (d, 8.8 Hz, 1-H) ppm (CDCl$_3$).

EXAMPLE 3 (=J 989)

Preparation of 16α,17β-dihydroxy-estra-1,3,5(10)-trien-3-yl N,N-dimethylsulfamate 120 ml of water, 1.58 g of benzyltriethylammonium chloride, 7.44 ml of N,N-dimethylamidosulphonyl chloride and 4 ml of 40% sodium hydroxide solution are agitated and added at a temperature of 80° C. to a solution of 2 g of estriol in 800 ml of toluene. Heating is continued to 80° C. The pH value 10 of the reactive solution is maintained in the course of that process by addition of 40% sodium hydroxide solution. Completion of reaction of all initial compounds is followed by cooling to room temperature and by work-up as described in Example 1. The residue thus obtained is recrystallised from acetone/n-hexane to give the title compound.

Melting point: 180–181° C.; $^1$H-NMR: 0.67 (s, 18-H), 2.89 (s, CH$_3$—N), 3.32 (m, 17-H), 3.84 (m, 16-H), 4.64, 4.71 (d each, 4.9 Hz, OH each), 7.34 (d, 8.8 Hz, 1-H) ppm (D$_6$-DMSO).

EXAMPLE 4 (=J 982)

Preparation of 17β-hydroxy-14α,15α-methylene-estra-1,3,5(10)-trien-3-yl N,N-dimethylsulfamate Reaction is performed, as described in Example 1, in a mixture of 30 ml of dichloromethane and 6.6 ml of water, between 1 g of 14α,15α-methylene-estra-1,3,5(10)-trien, 3,17β-diol, 2.4 g of sodium hydroxide, 0.24 g of triethylbenzylammnonium chloride and 3.6 ml of N,N-dimethylamidosulphonyl chloride. The title compound is obtained, following work-up, chromatographic purification and recrystallisation of the reaction product from acetone.

Melting point: 193–196° C.; $^1$H-NMR: 0.255 (m, CH$_2$), 0.99 (s, 18-H), 2.98 (s, CH$_3$—N), 3.55 (dd, E16 Hz, 17-H), 7.32 (d, 8.6 Hz, 1-H) ppm (CDCl$_3$).

EXAMPLE 5 (=J 984)

Preparation of 16α,17β-dihydroxy-estra-1,3,5(10)-trien-3-yl N,N-diethylsulfamate Reaction is performed, as described in Example 1, in a mixture of 800 ml of toluene and 128 ml of water, between 2 g of estriol, 5.2 g of sodium hydroxide, 1.72 g of triethylbenzylammonium chloride and 9.75 ml of N,N-diethylamidosulphonyl chloride. The title compound is obtained, following work-up, chromatographic purification and recrystallisation from acetone. Melting point: 121–124° C.; $^1$H-NMR: 0.67 (s, 18-H), 1.11 (t, 7.1 Hz, CH$_3$—CH$_2$—N), 3.33 (q, 7.1 Hz, CH$_3$—CH$_2$—N), 3.83 (m, 16-H), 4.65, 4.72 (all d, 4 Hz, 3.5 Hz, 16-OH, 17-OH), 7.33 (d, 8.4 Hz, 1-H) ppm (D$_6$-DMSO).

EXAMPLE 6

General manufacturing specifications for N-monosubstituted and N-unsubstituted 3-sulfamates of estra-1,3,5(10)-trien derivatives. A base (triethylamine or 2,6-di-tert. butyl-4-methylpyridine) and monosubstituted or N-unsubstituted amidosulphonyl chloride are agitated and added one by one to a solution of estra-1,3,5(10)-trien derivative in an appropriate solvent (dichloromethane, pyridine or dimethyl-formamide). The reaction temperature should not exceed +20° C. Complete conversion of the parent material is recordable by means of thin-layer chromatography, after one to three hours. For processing, the reactive solution is washed in diluted aqueous hydrochloric acid, saturated aqueous sodium hydrogencarbonate solution and water and is dried above anhydrous sodium sulphate and is evaporated to dryness in a rotary vacuum evaporator. The residue is purified over silica gel and/or by recrystallisation by means of column chromatography.

EXAMPLE 7 (=J 1044)

Preparation of 14α,15α-methylene estradiol 3-(N-methyl)sulfamate

Reaction is performed, as described in Example 6, in a solution of pyridine (12.7 ml) and 2,6-di-tert. butyl-4-methylpyridine (5.1 g), between methylene estrone (1.17 g) and (N-methyl)amidosulphonyl chloride (1 ml). The crude product, following work-up, is purified by column chromatography (chloroform/ethyl acetate 9/1) and is recrystallised from acetone/n-hexane to give 14α,15α-methylene estrone-(N-methyl)sulfamate. Argon shielding, exclusion of moisture and agitation are the conditions under which a borane solution (25 ml), prepared from sodium boron hydride (1 g) and boron trifluoride-diethylether complex (3.5 ml) in tetrahydrofurane (44 ml), are added in portions, at 0° C. to +5° C., to a solution of 14α,15α-methylene estrone-(N-methyl) amidosulphonate (809.5 mg) in tetrahydrofurane (15 ml). The reactive solution is allowed to stand for 20 hours at 0° C. to +5° C., before it is dripped into iced water. The title compound is obtained, following work-up, column chromatography (chloroform/ethyl acetate 9/1) and recrystallisation from acetone.

Melting point: 192–193.5° C.; $^1$H-NMR: 0.20 (m, $CH_2$), 0.2555 (m, $CH_2$), 0.89 (s, H-18), 2.71 (d, 3.8 Hz, $CH_3$—NH), 3.43 (m, H-17), 4.43 (d, 5.3 Hz, OH), 7.39 (d, 8.5 Hz, H-1), 8.12 (m, NH) ppm ($D_6$-DMSO).

EXAMPLE 8 (=J 1011)

Preparation of estrone-(N-methyl)sulfamate

Reaction is performed, as described in Example 6, of estrone (3 g) in a solution of dichloromethane (1200 ml) and triethylamine (28.2 ml) with N-methylamido-sulphonyl chloride (3 ml). The crude product, following work-up, is recrystallised from acetone/n-hexane to give the title compound.

Melting point: 192.5–196.5° C.; $^1$H-NMR: 0.91 (s, H-18), 2.95 (d, 5.1 Hz, $CH_3$—NH), 4.58 (m, NH), 7.30 (d, 8.2 Hz, H-1) ppm ($CDCl_3$).

EXAMPLE 9 (=J 1012)

Preparation of estradiol-(N-methyl)sulfamate

Estrone-(N-methyl)amidosulphonate (1 g) is reduced with sodium boron hydride (624.2 mg) in a mixture of tetrahydrofurane (20 ml) and methanol (20 ml). The crude product, following work-up, is recrystallised from acetone/n-hexane to give the title compound.

Melting point: 194–198.5° C.; $^1$H-NMR: 0.78 (s, H-18), 2.94 (d, 5.2 Hz, $CH_3$—NH), 4.53 (m, NH), 3.73 (dd, E16.9 Hz, H-17), 7.30 (d, 8.4 Hz, H-1) ppm ($CDCl_3$).

EXAMPLE 10 (=J 1036)

Preparation of 17α-ethinyl estradiol-3-(N-methyl)-sulfamate. Reaction is induced, as described in Example 6, of 17α-ethinyl estradiol-17-trimethylsilylether (1 g) in a solution of dichloromethane (25 ml) and 2,6-di-tert. butyl4-methylpyridine (3.3 g) with (N-methyl)amidosulphonyl chloride (0.72 ml). The reactive solution is processed by agitation for five hours in aqueous 1:1 diluted hydrochloric acid unto complete cleavage of the silylether, whereafter the crude product is purified by column chromatography (toluene/chloroform/methanol 80/15/5) and is recrystallised from acetone/n-hexane to give the title compound.

Melting point: 156–162.5° C.; $^1$H-NMR: 0.88 (s, H-18), 2.61 (s, =CH), 2.94 (d, 5.2 Hz, $CH_3$—NH), 4.53 (m, NH), 7.31 (d, 8.8 Hz, H-1) ppm ($CDCl_3$).

EXAMPLE 11 (=J 994)

Preparation of estrone-sulfamate.

Estrone (1 g) is dissolved in dimethylformamide (20 ml). Amidosulphonyl chloride (2.14 g) is then added to that solution. Agitation for six hours is followed by precipitation in water, and the product is recrystallised from ethyl acetate to obtain the title compound.

Melting point: 199–202° C.; $^1$H-NMR: 0.83 (s, H-18), 7.35 (d, 8.7 Hz, H-1), 7.9 (s, $NH_2$) ppm ($D_6$-DMSO).

EXAMPLE 12 (=J 995)

Preparation of estradiol-3-sulfamate

Estrone-sulfamate (1.4 g) is reduced with sodium boron hydride (960 mg) in a solution of tetrahydrofurane (28 ml) and methanol (28 ml). Work-up is followed by recrystallisation of the crude product from acetone to give the title compound.

Melting point: 211–213° C.; $^1$H-NMR: 0.67 (s, H-18), 3.53 (t, d 7.9 Hz, 4.7 Hz, H-17), 4.55 (d, 4.8 Hz, OH), 7.34 (d, 8.6 Hz, H-1), 7.90 (s, $NH_2$) ppm ($D_6$-DMSO).

EXAMPLE 13 (=J 1018)

Preparation of 14α,15α-methylene estradiol-3-sulfamate

Reaction is performed, as described in Example 6, of 14α,15α-methylene-estradiol-17-tert. butyldimethylsilylether (100 mg) in a solution of dichloromethane (3 ml) and 2.6di-tert. butyl-4-methylpyridine (180 mg) with amidosulphonyl chloride (145 mg). The crude product, following work-up, is purified by column chromatography (toluene/acetone 4/1) and is recrystallised from acetone/n-hexane, so that 14α,15α-methylene-17β-tert. butyldimethylsilyloxy-estra-1,3,5(10)-trien-3-yl-sulfamate is obtained. 14α, 15α-methylene-17β-tert. butyl-dimethylsilyloxy-estra-1,3,5(10)-trien-3-yl-sulfamate (2.2 g) is dissolved in tetrahydrofurane (100 ml). A mixture of acetic acid/water/tetrahydrofurane 3/1/1 (220 ml) is added to that solution. The reactive solution is allowed to stand for seven days at room temperature before work-up, purification of the product by column chromatography (cyclohexane/ethyl acetate 3/2) and recrystallisation from acetone/n-hexane.

Melting point: 210–214° C.; $^1$H-NMR: 0.20 (m, $CH_2$), 0.26 (m, $CH_2$), 0.89 (s, H-18), 3.4 (m, H-17), 4.41 (d, 5.2 Hz, OH) 7.39 (d, 8.8 Hz, H-1), 7.90 (s, $NH_2$) ppm ($D_6$-DMSO).

EXAMPLE 14 (=J 1028)

Preparation of 17α-ethinylestradiol-3-sulfamate

Reaction is performed, as described in Example 6, of 17α-ethinylestradiol-17-trimethylsilylether (1.5 g) in a solution of dichloromethane (40 ml) and triethylamine (16 ml) with amidosulphonyl chloride (8 g). The crude product, following breakdown of the silylether group and work-up, is purified by column chromatography (chloroform/ethyl acetate 7/3) and is recrystallised from acetone/n-hexane to give the title compound. Melting point: 209–211° C.; $^1$H-NMR: 0.76 (s, H-18), 3.35 (s, =CH), 5.35 (s, OH), 7.35 (d, 8.7 Hz, H-1), 7.89 (s, NH$_2$) ppm (D$_6$-DMSO).

EXAMPLE 15 (=J 1034)

Preparation of estriol-3-sulfamate

Reaction is performed, as described in Example 6, of estriol-16,17-bis-tert. butyl-dimethylsilylether (2 g) in a solution of dichloromethane (13 ml) and triethylamine (15.5 ml) with amidosulphonyl chloride (7.9 g). The crude product, following work-up, is subjected to silylether cleavage, according to Example 13, whereafter the isolated substance is purified by column chromatography (chloroform/methanol/acetic acid 90/13/1) and is recrystallised from acetone/n-hexane to give the title compound.

Melting point: 208–213° C.; $^1$H-NMR: 0.67 (s, H-18), 3.30 (m, H-17), 3.84 (m, H-16), 4.7 (m, OH), 7.32 (d, 8.4 Hz, H-1) ppm (D$_6$-DMSO).

EXAMPLE 16 (=J 1040)

Preparation of estriol-3-(N-methyl)sulfamate

Reaction is performed, as described in Example 6, of estriol-16,17-bis-tert. butyl-dimethylsilylether (1.7 g) in a solution of dichloromethane (51 ml) and 2,6-di-tert. butyl-4-methylpyridine (4.05 g) with (N-methyl)-amidosulphonyl chloride (0.87 ml). The crude product, following work-up, is purified by column chromatography (toluene/chloroform/methanol 80/15/5) and is subsequently subjected to silylether cleavage, according to Example 13. The title compound was obtained from column chromatography of the isolated substance (chloroform/methanol/acetic acid 90/13/1) and recrystallisation from acetone/n-hexane.

Melting point: 199–202° C.; $^1$H—NMR: 0.67 (s, H-18), 2.70 (s, NH-CH$_3$), 3.30 (m, H-17), 3.84 (m, H-16), 4.7 (m, OH), 7.33 (d, 8.7 Hz, H-1) ppm (D$_6$-DMSO).

EXAMPLE 17 (=J 1050)

Preparation of 17α-estradiol-3-sulfamate

Reaction is performed, as described in Example 6, of 17α-estradiol-tert. butyl-dimethylsilylether (1.94 g) in a solution of dichloromethane (70 ml) and 2.6-di-tert. butyl-4-methylpyridine (3.6 g) with amidosulphonyl chloride (2.75 g). The crude product, following work-up, is purified by column chromatography (toluene/acetone 4/1) and is recrystallised from acetone/n-hexane. The 17α-tert. butyl-dimethylsilyloxy-estra- 1,3,5(10)-trien-3-yl-sulfamate thus obtained is subjected to silylether cleavage according to Example 13. The title compound was obtained from column chromatography of the isolated substance (toluene/ethyl acetate/chloroform 6/3/1) and recrystallisation from acetone/n-hexane.

Melting point: 192–196° C.; $^1$H-NMR: 0.62 (s, H-18), 3.59 (d, 5.5 Hz, H-17), 7.36 (d, 8.8 Hz, H-1), 7.88 (s, NH$_2$) ppm (D$_6$-DMSO).

EXAMPLE 18 (=J 1010)

Preparation of 14α,15α-methylene-estrone-sulfamate

Reaction is performed, as described in Example 6, of 14α,15α-methylene-estrone (765 mg) in a solution of dichloromethane (50 ml) and triethylamine (7.7 ml) with amidosulphonyl chloride (11.7 g). The crude product, following work-up, is purified by column chromatography (chloroform/ethyl acetate 9/1) and is recrystallised from acetone/n-hexane, so that the title compound is obtained.

Melting point: 191–195° C.; $^1$H-NMR: −0.40 (m, CH$_2$), 0.80 (m, CH$_2$), 1.12 (s, H-18), 7.40 (d, 8 Hz, H-1), 7.93 (s, NH$_2$) ppm (D$_6$-DMSO).

EXAMPLE 19 (=J 1021)

Preparation of 11β-methoxyestrone-sulfamate

Sodium hydride is added in portions (0.4 g, 80%) to a solution of 11β-methoxyestrone (2 g) in dimethylformamide (37 ml). On completion of evolution of hydrogen, amidosulphonyl chloride (6.2 g) is added, and the reactive mixture is agitated overnight at room temperature. It is then precipitated in water, and the product is purified by column chromatography (chloroform/acetone 7/3). The title compound is obtained from recrystallisation from acetone/n-hexane.

Melting point: 191–195° C.; $^1$H-NMR: 0.99 (s, H-18), 3.20 (s, CH$_3$O), 4.24 (m, H-11), 7.26 (d, 8.7 Hz, H-1), 7.93 (s, NH$_2$) ppm (D$_6$-DMSO).

EXAMPLE 20 (=J 1038)

Preparation of estra-1,3,5(10)-trien-3, 17β-diyl-3-sulfamate, 17-pentanoate

Reaction is performed, as described in Example 6, of estradiol-17-pentanoate (2 g), dissolved in dimethylformamide (37 ml), with sodium hydride (336 mg, 80%) and amidosulphonyl chloride (6.47 g). The title compound is obtained, following work-up, column chromatography (chloroform/ethyl acetate 9/1) and recrystallisation from acetone/n-hexane.

Melting point: 107–108° C.; $^1$H-NMR: 0.78 (s, H-18), 0.87 (t, 7.3 Hz, CH$_3$(CH$_2$)$_3$—CO), 2.29 (t, 7.2 Hz, C$_3$H$_7$—CH$_2$—CO), 4.63 (dd, E15.5 Hz, H-17), 7.34 (d, 8.4 Hz, H-1), 7.89 (s, NH$_2$) ppm (D$_6$-DMSO).

EXAMPLE 21 (=J 1051)

Preparation of 17α-hydroxy-14α,15α-methylene-estra-1,3,5(10), 8-tetraene-3-yl-sulfamate Reaction is performed, as described in Example 6, of 14α,15α-methylene-17α-trimethylsilyloxy-estra-1,3,5(10)-trien-3-ol (100 mg) in a solution of dichloromethane (3 ml) and 2.6-di-tert. butyl4-methylpyridine (180 mg) with amidosulphonyl chloride (145 mg). The crude product, following cleavage of the silylether group and work-up, is purified by column chromatography (cyclohexane/ethyl acetate 3/2) and is recrystallised from acetone/n-hexane.

White foam; Fp 189–194° C., $^1$H-NMR: 0.46 (m, CH$_2$), 0.92 (s, H-18), 1.28 (m, CH$_2$), 3.90 (d, E6.0 Hz, H-17) ppm (CDCl$_3$), 7.35 (d, 8.8 Hz, H-1), 7.88 (s, NH) ppm (D$_6$-DMSO).

EXAMPLE 22 (=J 992)

Preparation of estrone-(N,N-dimethyl)sulfamate

Estrone (1 g) together with dichloromethane (30 ml), water (3 ml), benzyl-triethylammonium chloride (0.24 g), N,N-dimethylamidosulphonyl chloride (3.6 ml) and sodium hydroxide solution (40%, 6 ml) is agitated at room temperature for two hours. This is followed by work-up, according to Example 1, and the product is recrystallised from ethyl acetate.

Melting point: 192–194° C.; $^1$H-NMR: 0.91 (s, H-18), 2.98 (s, N—CH$_3$), 7.28 (d, 9.9 Hz, H-1) ppm (CDCl$_3$).

EXAMPLE 23 (=J 991)

Preparation of estradiol-3-(N,N-dimethyl)sulfamate

Reaction of estradiol (1 g) is performed, as described in Example 22. Work-up is followed by recrystallisation of the product from chloroform/methanol.

Melting point: 204–208° C.; $^1$H-NMR: 0.78 (s, H-18), 2.98 (s, N—CH$_3$), 3.72 (dd, E16 Hz), 7.28 (d, 9.9 Hz, H-1) ppm (CDCl$_3$).

EXAMPLE 24 (=J 1052)

Preparation of 14α,15α-methylene-estradiol-3-pyrrolidinosulphonate

Reaction is performed, as described in Example 22, between 14α,15α-methylene-estradiol (1.05 g) and dichloromethane (30 ml), water (3 ml), benzyltriethyl-ammonium chloride (0.24 g), pyrrolidinosulphonyl chloride (4.5 ml) and sodium hydroxide solution (40%, 8 ml). The title compound is obtained, following work-up, according to Example 1.

Amorphous solid substance; $^1$H-NMR: 0.20 (m, CH$_2$), 0.26 (m, CH$_2$), 0.89 (s, H-18), 3.33 (m, —CH$_2$—N—CH$_2$—), 3.4 (m, H-17), 4.41 (d, 5.2 Hz, OH), 7.36 (d, 8.7 Hz, H-1) ppm (D$_6$-DMSO).

EXAMPLE 25 (=J 1053)

Preparation of estriol-3-morpholinosulphonate

Reaction is performed, according to Example 3, of estriol (2 g) in a mixture of toluene (800 ml) and water (120 ml) with morpholinosulphonyl chloride (9.2 ml), benzyltriethylammonium chloride (1.58 g) and sodium hydroxide solution (40%, 6.5 ml). The title compound is obtained, following work-up, according to Example 1.

Melting point: 188–192° C.; $^1$H-NMR: 0.67 (s, H-18), 3.28–3.36 (m, H-17, —CH2—N—CH2—), 3.65–3.68 (m, —CH2—O—CH2—), 4.7 (m, OH), 7.37 (d, 8.8 Hz, H-1) ppm (D$_6$-DMSO).

EXAMPLE 26 (=J 1054)

Preparation of equilenine-sulphamate

Equilenine (1 g) is esterified with amidosulphonyl chloride in dimethylformamide solution, as described in Example 11, and is worked-up.

Slightly yellowish resin; $^1$H-NMR: 0.69 (s, H-18), 7.23, 756 (d, 8.4 Hz, d, 8.5 Hz, H-6 and H-7), 7.82 (d, 9.8 Hz, H-1), 7.9 (s, NH$_2$) ppm (D$_6$-DMSO).

It is claimed:

1. A process for preparing estra-1,3,5(10)-trien compounds selected from the group consisting of:
17β-hydroxy-14α,15α-methylene-estra-1,3,5(10)-trien-3-yl N,N-dimethyl-sulfamate,
17β-hydroxy-14α,15α-methylene-estra-1,3,5(10)-trien-3-yl N-methyl-sulfamate,
17β-hydroxy-14α,15α-methylene-estra-1,3,5(10)-trien-3-yl sulfa-mate,
17β-hydroxy-14α,15α-methylene-estra-1,3,5(10),7-tetraene-3-yl N,N-dimethylsulfamate,
17β-hydroxy-14α,15α-methylene-estra-1,3,5(10),8-tetraene-3-yl N,N-dimethylsulfamate,
17β-hydroxy-14α,17α-vinylene-estra-1,3,5(10)-trien-3-yl N,N-dimethylsulfamate,
17β-hydroxy-11β-methoxy-19-nor-17α-pregn-1,3,5(10)-trien-20-in-3-yl N,N-dimethylsulfamate,
11β-methoxy-17-oxo-estra-1,3,5(10)-trien-3-yl sulfamate,
17β-hydroxy-estra-1,3,5(10)-trien-3-yl N-methylsulfamate,
17β-hydroxy-estra-1,3,5(10)-trien-3-yl sulfamate,
17β-hydroxy-estra-1,3,5(10), 6,8-pentaene-3-yl sulfamate,
17β-hydroxy-estra-1,3,5(10)-trien-3-yl sulfamate,
16α,17β-dihydroxy-estra-1,3,5(10)-trien-3-yl N,N-dimethyl-sulfamate,
16α,17β-dihydroxy-estra-1,3,5(10)-trien-3-yl N-methysulfamate,
16α,17β-dihydroxy-estra-1,3,5(10)-trien-3-yl sulfamate,
17β-hydroxy-14α,17α-vinylene-estra-1,3,5(10)-trien-3-yl sulfamate,
14α,17α-ethylene-17β-hydroxy-estra-1,3,5(10)-trien-3-yl N-methyl-sulfamate,
16α,17α-dihydroxy14α, 17α-ethylene-estra-1,3,5(10)-trien-3-yl sulfamate, and
17β-hydroxy-11β-methoxy-19-nor-17α-pregn-1,3,5(10)-trien-20-in-3-yl sulfamate, wherein said process comprises reacting an estra-1,3,5(10)-trien-3-ol in a manner known per se with an appropriately substituted amidosulphonyl chloride to obtain the esterification of the 3-OH group of estra-1,3,5(10)-trien compounds.

2. Pharmaceutical compositions containing estra-1,3,5(10)-trien compounds selected from the group consisting of:
17β-hydroxy-14α,15α-methylene-estra-1,3,5(10)-trien-3-yl N,N-dimethyl-sulfamate,
17β-hydroxy-14α,15α-methylene-estra-1,3,5(10)-trien-3-yl N-methyl-sulfamate,
17β-hydroxy-14α,15α-methylene-estra-1,3,5(10)-trien-3-yl sulfamate,
17β-hydroxy-14α,15α-methylene-estra-1,3,5(10), 7-tetraene-3-yl N,N-dimethylsulfamate,
17β-hydroxy-14α,15α-methylene-estra-1,3,5(10), 8-tetraene-3-yl N,N-dimethylsulfamate,
17β-hydroxy-14α,17α-vinylene-estra-1,3,5(10)-trien-3-yl N,N-dimethylsulfamate,
17β-hydroxy-11β-methoxy-19-nor-17α-pregn-1,3,5(10)-trien-20-in-3-yl N,N-dimethylsulfamate,
11β-methoxy-17-oxo-estra-1,3,5(10)-trien-3-yl sulfamate,
17β-hydroxy-estra-1,3,5(10)-trien-3-yl N-methylsulfamate,
17β-hydroxy-estra-1,3,5(10)-trien-3-yl sulfamate,
17β-hydroxy-estra-1,3,5(10), 6,8-pentaene-3-yl sulfamate,
17β-hydroxy-estra-1,3,5(10)-trien-3-yl sulfamate,
16α,17β-dihydroxy-estra-1,3,5(10)-trien-3-yl N,N-dimethyl-sulfamate,
16α,17β-dihydroxy-estra-1,3,5(10)-trien-3-yl N-methylsulfamate,
16α,17β-dihydroxy-estra-1,3,5(10)-trien-3-yl sulfamate,
17α-hydroxy-14α,17α-vinylene-estra-1,3,5(10)-trien-3-yl sulfamate,
14α,17α-ethylene-17β-hydroxy-estra-1,3,5(10)-trien-3-yl N-methyl-sulfamate,
16α,17β-dihydroxy 14α,17α-ethylene-estra-1,3,5(10)-trien-3-yl sulfamate, and
17β-hydroxy-11β-methoxy-19-nor-17α-pregn-1,3,5(10)-trien-20-in-3-yl sulfamate, said pharmaceutical compositions optionally combined with pharmaceutically safe adjuvants and carriers.

3. Estra-1,3,5(10)-trien compounds selected from the group consisting of:

17β-hydroxy-14α,15α-methylene-estra-1,3,5(10)-trien-3-yl N,N-dimethyl-sulfamate, 17β-hydroxy-14α,15α-methylene-estra-1,3,5(10)-trien-3-yl N-methyl-sulfamate, 17β-hydroxy-14α,15α-methylene-estra-1,3,5(10)-trien-3-yl sulfamate, 17β-hydroxy-14α,15α-methylene-estra-1,3,5(10),7-tetraene-3-yl N,N-dimethylsulfamate, 17β-hydroxy-14α,15α-methylene-estra-1,3,5(10),8-tetraene-3-yl N,N-dimethylsulfamate, 17β-hydroxy-14α,17α-vinylene-estra-1,3,5(10)-trien-3-yl N,N-dimethylsulfamate, 17β-hydroxy-14α,17α-vinylene-estra-1,3,5 (10)-trien-3-yl sulfamate, 17β-hydroxy-11β-methoxy-19-nor-17α-pregn-1,3,5(10)-trien-20-in-3-yl N,N-dimethylsulfamate, 11β-methoxy-17-oxo-estra-1,3,5(10)-trien-3-yl sulfamate, 17β-hydroxy-estra-1,3,5(10)-trien-3-yl N-methylsulfamate, 17β-hydroxy-estra-1,3,5(10)-trien-3-yl sulfamate, 17β-hydroxy-estra-1,3,5(10), 6,8-pentaene-3-yl sulfamate, 17α-hydroxy-estra-1,3,5(10)-trien-3-yl sulfamate, 16α,17β-dihydroxy-estra-1,3,5(10)-trien-3-yl N,N-dimethyl-sulfamate, 16α,17β-dihydroxy-estra-1,3,5(10)-trien-3-yl N-methylsulfamate, 16α,17β-dihydroxy-estra-1,3,5(10)-trien-3-yl sulfamate, 16α,17β-dihydroxy 14α,17α-ethylene-estra-1,3,5(10)-trien-3-yl sulfamate, 14α,17α-ethylene-17β-hydroxy-estra-1,3,5(10)-trien-3-yl N-methyl-sulfamate, and 17β-hydroxy-11β-methoxy-19-nor-17α-pregn-1,3,5(10)-trien-20-in-3-yl sulfamate.

* * * * *